United States Patent [19]

Lam

[11] Patent Number: 5,225,323
[45] Date of Patent: Jul. 6, 1993

[54] HUMAN HIGH-AFFINITY NEUROTRANSMITTER UPTAKE SYSTEM

[75] Inventor: Dominic M. Lam, Woodlands, Tex.

[73] Assignee: Baylor College of Medicine, Houston, Tex.

[21] Appl. No.: 342,238

[22] Filed: Apr. 24, 1989

Related U.S. Application Data

[63] Continuation-in-part of Ser. No. 274,328, Nov. 21, 1988, Pat. No. 5,188,954.

[51] Int. Cl.$^5$ .............................................. C12Q 1/68
[52] U.S. Cl. .................................... 435/6; 435/29; 435/69.1; 435/70.1; 435/70.3; 435/240.1; 435/240.2; 435/240.23; 435/172.3; 435/284; 514/44; 536/23.5; 935/9; 935/11; 935/13; 935/34; 935/70; 935/71; 935/78; 935/88
[58] Field of Search ................. 435/6, 29, 172.3, 69.1, 435/70.1, 70.3, 240.1, 240.2, 240.23, 284; 436/501; 536/27, 28, 29; 935/78, 9, 11, 13, 34, 70, 71, 88; 514/44

[56] References Cited

U.S. PATENT DOCUMENTS 4,675,285  1/1987  Clark et al. ............................. 435/6
4,985,352  1/1991  Julius et al. ............................ 435/6

OTHER PUBLICATIONS

Lowe et al. (1988) Journal of Cell Biology, vol. 106, pp. 51–59.
Yorek et al. (1987) Journal of Biological Chemistry, vol. 262, No. 23, pp. 10986–10993.
Blin et al.; "A General Method for Isolation of High Molecular Weight DNA from Eukaryotes"; Nucleic Acids Research; vol. 3, No. 9, Sep. 1976, pp. 2303–2308.
Claudio et al; "Genetic Reconstitution of Functional Acteylcholine Receptor Channels in Mouse Fibroblasts"; Science, vol. 238, Dec. 1987, pp. 1688–1694.
Fargin et al; "The Genomic Clone G-21 Which Resembles a Betz-Adrenergic Receptor Sequence Enclodes the 5-Ht Receptor"; Nature; vol. 335, Sep. 1988, pp. 358–360.
Frnka et al; "Pharmacological Characteristics of High-Affinity Serotonin Uptake Systems Established Through Gene Transfer"; The Hournal of Pharmacology and Experimental Therapeutics; vol. 256, No. 2, pp. 734–740.
Julius et al., "Molecular Characterization of a Functional cDNA Encoding the Serotonin Ic Receptor"; Science, vol. 241, pp. 558–564.
Old, R. W., "Principles of Gene Manipulation" (1985) 2, pp. 231–254, Blackwell Scientific Publications, London.
Yorek et al., "Synthesis and High Affinity Uptake of Serotonin and Dopamine by Human Y79 Retinoblastoma Cells" (Dec. 1, 1987) Biological Abstracts, 84(11) Abstract No. 124514.
Allen et al., "Isoproterenol response following transfection of the mouse $\beta_2$-adrenergic receptor gene into Y1 cells", EMBO Journal (1988) 7:133–138.
Asano et al., "Rabbit Brain Glucose Transporter Responds to Insulin When Expressed in Insulin-sensitive Chinese Hamster Ovary Cells", The Journal of Biological Chemistry (1989) 264:3416–3420.
Blakely, et al., "Expression of neurotransmitter transport from rat brain mRNA in Xenopus laevis oocytes", Proc. Natl. Acad. Sci. USA (1988) 85:9846–9850.

(List continued on next page.)

Primary Examiner—Amelia Burgess Yarbrough
Assistant Examiner—Ardin H. Marschel
Attorney, Agent, or Firm—Barbara Rae-Venter

[57] ABSTRACT

Non-primate or primate cells are provided comprising a functional human transporter for neurotransmitter uptake. The cells allow for dissection of the mechanism of neurotransmitter transport, as well as screening for agonists and antagonists of the neurotransmitter with respect to its uptake. Methods are provided for producing such cells. Specifically, the cells are transformed with human DNA comprising the gene encoding for the neurotransmitter transporter, Whereby this protein(s) is expressed and transported to the membrane and is capable of functioning to transfer the neurotransmitter from the extracellular space intracellularly.

17 Claims, No Drawings

OTHER PUBLICATIONS

Burch and McBride, "Human Gene Expression in Rodent Cells after Uptake of Isolated Metaphase Chromosomes", *Proc. Nat. Acad. Sci. USA* (1975) 72:1797–1801.

Burk et al., "cDNA Cloning, Functional Expression, and mRNA Tissue Distribution of a Third Organellar $Ca^{2+}$ Pump", *The Journal of Biological Chemistry* (1989) 264:18561–18568.

Change et al., "Characterization of a genetically reconstituted high-affinity system for serotonin transport", *Proc. Natl. Acad. Sci. USA* (1989) 86:9611–9615.

Fraser et al., "Continuous High Density Expression of Human $\beta_2$-Adrenergic Receptors in a Mouse Cell Line Previously Lacking $\beta$-Receptors", *The Journal of Biological Chemistry* (1987) 262:14843–14846.

Hara et al., "Expression of sodium pump activities in BALB/c3T3 cells transfected with cDNA encoding $\alpha_3$-subunits of rat brain $Na^+$, $K^+$-ATPase", *FEBS* (1988) 238:27–30.

Jones et al., "Electrophysiological characterization of cloned m1 muscarinic receptors expressed in A9 L cells", *Proc. Natl. Acad. Sci. USA* (1988) 85:4056–4060.

Sardet et al., "Molecular Cloning, Primary Structure, and Expression of the Human Growth Factor-Activatable $Na^+/H^+$ Antiporter", *Cell* (1989) 56:271–280.

Sarthy, "$\gamma$-Aminobutyric acid (GABA) uptake by Xenopus occytes injected with rat brain mRNA" Molecular Brain Research (1986) 1:97–100.

Takeyasu et al., "Ouabain-sensitive $Na^+ + K^+$-ATPase Activity Expressed in Mouse L Cells by Transfection with DNA Encoding the $\alpha$-Subunit of an Avian Sodium Pump", The Journal of Biological Chemistry (1988) 263:4347–4354.

Underhill and Flintoff, "Complementation of a Methotrexate Uptake Defect in Chinese Hamster Ovary Cells by DNA-Mediated Gene Transfer", *Molecular and Cellular Biology* (1989) 9:1754–1758.

Dingledine et al., "Amino Acid Receptors and Uptake in the Mammalian Central Nervous System", *CRC Critical Reviews of Neurology* (1988) 4, (1) pp. 1–96.

Kuhn, et al. (1983), *Mol. Biol. Med.* 1:335–352.

Chao, et al. (1986), *Science* 232:518–521.

Greco, et al. (1987), *Proc. Natl. Acad. Sci. USA* 84:1565–1569.

Southern and Berg, *J. Molec. Appl. Genet.* (1982) 1:327–341.

HUMAN HIGH-AFFINITY NEUROTRANSMITTER UPTAKE SYSTEM

This invention was made with government support under NIH Grant No. EY02423 awarded by the National Institutes of Health through the National Eye Institute. The government has certain rights in the invention.

This application is a continuation-in-part application of U.S. application Ser. No. 274,328 which was filed Nov. 21, 1988, and now U.S. Pat. No. 5,188,954.

INTRODUCTION

1. Technical Field

This invention relates to high-affinity human neurotransmitter transporters introduced into cultured cells and methods of use of these cells, in particular for identifying agonists and antagonists of the neurotransmitter transporters.

2. Background

An essential regulatory step in neurotransmission in both the central and peripheral nervous systems is the inactivation of the neurotransmitter following its release into the synaptic cleft. For biogenic amine and amino acid neurotransmitters, uptake of the released neurotransmitter is the most common mechanism for inactivation. In the central nervous system, the uptake is accomplished by glial cells and/or by the reuptake system (transporters) of the presynaptic neuron. These transporters, which reduce intersynaptic concentration of neurotransmitters, are characteristically ion dependent, of high affinity, and are temperature sensitive.

Amelioration of various nervous disorder symptoms frequently involves manipulation of transmitter levels is the affected tissues(s). One of these manipulations involves the use of pharmaceutical agents to inhibit the reuptake of the appropriate transmitter(s). For example, serotonin and norepinephrine uptake blockers (e.g. imipramine) are used as antidepressants, and benztropine, an antagonist of dopamine uptake, temporarily alleviates the symptoms of Parkinson's disease. Application of an appropriate antagonist to block uptake prolongs and enhances the action of the neurotransmitter. However, methods for evaluating potential therapeutic agents are hampered by the lack of an adequate system for studying potential therapeutic agents in vitro.

Intact neural tissue, primary neuronal/glial cultures, neuroblastoma/glioma cell lines and synaptosomal and membrane vesicle preparations have been used to investigate in vitro the processes involved with neuronal uptake. However, these systems suffer from substantial limitations, including the difficulty in establishing systems which are homogenous in both neurochemical and neurophysiological composition, well defined in terms of growth and maintenance requirements, and neurophysiologically and neurochemically stable over time. They also do not lend themseleves readily to operation on a large scale. Other methods used for screening of potential therapeutic agents include the use of membrane receptor assays. Therefore, it is of interest to develop an in vitro system which can be used to investigate the mechanisms of transmitter-specific transport (uptake) systems, as well as to evaluate potential agonists and antagonists of the uptake system, particularly where the system is relatively insulated from other cellular components which may compete for binding and/or transport of the agent under investigation.

RELEVANT LITERATURE

The expression of exogenously introduced DNA has been described for established cell lines by Wigler et al, *Cell* (1979) 16:777-785; Kuhn, et al., *Mol. Biol. Med.* (1983) 1:335-352; Chao, et al., *Science* (1986) 232:418-421; and Greco, et al., *Proc. Natl. Acad. Sci. USA* (1987) 84:1565-1569. Transformation of mouse cells with plasmids comprising a viral transfection system is described by Southern and Berg, *J. Mol. Appl. Genet.* (1982) 1:327-341.

SUMMARY OF THE INVENTION

Novel transgenic cell lines expressing neurotransmitter transporters and methods for their preparation are provided. Host cells capable of stable maintenance in culture are transformed with a DNA sequence encoding a neurotransmitter transporter. The resulting transgenic cells are characterized as being capable of specifically transporting a neurotransmitter of interest, with uptake of the neurotransmitter being ion dependent, saturable and temperature sensitive. The transgenic cells find use for screening potential agonists or antagonists of the neurotransmitter transporter.

DESCRIPTION OF THE SPECIFIC EMBODIMENTS

Transgenic cells, particularly mammalian cells, more particularly non-primate vertebrate cells, capable of stable growth in culture are provided which comprise a functional primate, particularly human, neurotransmitter uptake system (transporter). Methods are provided for preparing these cells, as well as for using the cells for investigation of neurotransmitter transport uptake mechanisms and screening for potential agonists and antagonists of a neurotransmitter of interest.

The host cells of this invention will, for the most part, be non-primate vertebrate cells derived from rodentiae, lagomorpha, equine, bovine, porcine and the like, more particularly murine tissues and organs. Cells of primate origin may also be used as host cells when appropriate. The host cells will generally be other than those associated with the brain (neurons, astrocytes, glial cells, and the like). Thus the cells may be derived from skin, for example fibroblasts; and may be epithelial cells derived from a variety of tissues and organs including muscle, bone, and the like. Cells of particular interest are those which under in vitro or culture conditions do not manifest high rates of genetic recombination, and which may be easily grown under the culture conditions such that they stably retain the exogenous DNA. Cell lines which may find use as host cells include mouse L-M fibroblasts, L-TK$^-$ fibroblasts, L-929 fibroblasts and 3T3 fibroblasts.

The neurotransmitter uptake systems or transporters which may be introduced into a host cell include the transporters for biogenic amines such as serotonin, dopamine, epinephrine, norepinephrine, and amino acids such as L-glycine and L-glutamic acid, and $\gamma$-aminobutyric acid. By "transporter" is meant a transporter which, under physiologic conditions of pH, temperature and the like, is specific for at least one neurotransmitter and in which uptake and accumulation of the neurotransmitter may be (a) inhibited by known agonists and antagonists of the neurotransmitter; (b) is ion and temperature dependent; (c) is saturable; and (d) is of high affinity. By high affinity is intended a Km of at most about $10^{-5}$M, preferably $10^{-6}$M to $10^7$M, more preferably $10^{-8}M$, for the endogenous neurotransmitter associated with the transporter.

The exogenous DNA encoding the transporter may be introduced into the host cell in a variety of ways. Conveniently, the host cell may be transformed with human genomic DNA encoding the transporter in the presence of a DNA sequence which provides for a selection marker. Thus, human genomic DNA may be prepared, as intact chromosomes or as degraded DNA fragments, having from about 5 to 100 kbp, and mixed with a plasmid or linear DNA capable of stable maintenance or integration into the genome of the host cell and carrying a selection marker. Conveniently, calcium phosphate precipitation may be employed as described in the literature. For example, the DNA may be dissolved in an appropriate phosphate buffered saline solution, about pH 7, and an equal volume of 0.1–0.5M calcium chloride added drop-wise. The precipitate is incubated, followed by adding to the cells and incubating for an extended period of time, usually for at least about eight hours and for not more than about 24 hours. The cells then are separated from the precipitate and cultured in the presence of a selection agent.

The particular manner of selection is not critical to this invention. For the most part resistance to cytotoxic agents is convenient. Various antibiotics may be employed, but particularly convenient combinations are a neomycin resistance gene APH(3')II with G418, or with appropriate cells, or the DHFR gene in combination with methotrexate. Resistant cells containing a specific transporter may be further identified by, for example, exposure to radiolabelled neurotransmitter following treatment with the cytotoxic agent. The selectable marker gene may be associated with a replication system, since the combination of the gene with a replication system generally provides for a larger number of transformed cells which may be selected. Various replication systems are available as derivatives of SV40, bovine papilloma virus, adenovirus, etc. These vectors find ample description in the literature.

Transformation with genomic DNA avoids the difficulties of identifying mRNA or the genomic sequence encoding the transporter. However, rather than transform the host cells with genomic DNA, one may transform with the appropriate transporter gene, where such gene is available. If such sequence is available, this sequence may then be used for transformation in accordance with known techniques. It may be desirable to replace the transcriptional initiation region of the transporter gene with a host cell transcriptional initiation region. In some cases this would not be desirable, for example, where the transporter transcriptional region is subject to different conditions for induction to those of the host cell transcriptional initiation region and it is of interest to determine the induction mechanism and/or the effect of compounds on such induction of expression of the transporter in its cell of origin. The joining of the transporter gene to a replication system and transformation of the host cells with the resulting plasmids is well known in the literature and the transporter gene could be introduced into a plasmid comprising a marker plasmid, so that the host cell would be simultaneously transformed with the marker and the transporter gene. Selection would follow in the same way as selection occurred for cotransfection of a marker plasmid and genomic DNA.

Transgenic cells can be selected based on resistance to the cytotoxic agent. Transformed colonies are exposed to the cytotoxic agent, followed by uptake of labelled, normally radioactively-labelled, neurotransmitter of interest. After contacting the transformed cell colonies with the labelled neurotransmitter, and incubating for sufficient time, usually from about 0.5 to about two hours at physiological temperature, the cells are thoroughly washed to remove any extracellular neurotransmitter. The presence of the neurotransmitter intracellularly may then be determined by means of the label. Conveniently, a radiolabel is employed. Desirably, the results from different colonies are normalized to correct for differences in the number of cells or levels of expression in individual cells, for example, by assaying for alkaline phosphatase activity or by protein quantitation.

In order to ensure that the neurotransmitter uptake is related to expression of the human transporter gene, the cell colonies may be further screened to demonstrate that the neurotransmitter uptake is dependent upon conditions and ancillary compounds associated with in vivo neurotransmitter uptake. For example, where the neurotransmitter is serotonin, which is both sodium ion dependent and temperature dependent, a showing of temperature and sodium dependence of serotonin uptake would be indicative of serotonin uptake by virtue of the presence of a serotonin transporter. In addition, one may employ agonists and antagonists of the transmitter, for example, use of imipramine which inhibits neuronal uptake of serotonin and demonstrate that the uptake is sensitive to the presence of agonists and is inhibited by antagonists. Furthermore, rigorous kinetic measurements can be employed to establish the affinity and capacity of the neurotransmitter uptake system as being in agreement with high-affinity uptake systems detected in vivo.

Once the cells have been identified as specifically transporting a particular neurotransmitter and that transport of the neurotransmitter is sensitive to the same agents and conditions associated with the neurotransmitter transporter present in humans, the cells may then be used in a wide variety of ways. The cells may be used in research for investigating the mechanism of the neurotransmitter interacting with its receptor. The host cell may additionally be transformed with other human genes(s) to determine what effect the expression of the additional human gene(s) has on the functioning of the neurotransmitter transporter. In this way, the presence of associations which may have specific effects on the functioning of the neurotransmitter transporter may be determined. One may relate changes in polarity of the cell, by identifying certain channels associated with the functioning of the cell. In addition, one may change the ionic strength in the medium in which the cell is grown or the concentration of a specific cation to investigate the various effects of the inorganic salts.

Of particular interest is the use of the transformed host cells for screening compounds for agonist or antagonist activity. Thus, by measuring the amount of neurotransmitter which is transported into the host cells in the presence or absence of the investigatory or candidate compound, one can evaluate the role of the compound. Agonists will be distinguished from antagonists, where transport of the neurotransmitter is associated with a specific function which is observable with the cell such as an increase or decrease in cyclic AMP or intracellular cation concentration. Where no such specific function occurs, then the compounds may be further screened with neurons or brain tissue to determine whether the compound is an agonist or antagonist. Thus, the subject transformed host cells provide for a rapid and efficient means for screening compounds which can competitively bind to the human neurotransmitter transporter, so as to compete for, and either prevent or enhance the binding or transport (uptake) of the natural neurotransmitter.

The invention now being generally described, the same will be better understood by reference to the following examples which are provided for purposes of illustration only and are not to be considered limiting of the invention unless so specified.

EXPERIMENTAL

Example I

Preparation Of Transgenic Cells Comprising Transporters

Calcium phosphate precipitation (Graham & Van der Eb (1973) *Virology* 52:456–467) is an efficient means of introducing exogenous DNA into mouse fibroblast L cells. This method was used to cotransfect into L-M cells human genomic DNA and pSV2neo, a neomycin resistance-bearing plasmid capable of rendering eukaryotic cells resistant to G418 (Southern & Berg (1982) *J. Mol. Appl. Genet.* 1:327–341). Our studies indicated that L-M cells were sensitive to the presence of 400 µg/ml G418 in the culture medium. This was the antibiotic concentration used to select for cell-transfectants, and gave rise to over 10,000 G418-resistant clones following one transfection experiment.

Mouse L-M fibroblast cells (ATCC CCL 1.2) were cultured in Dulbecco's Modified Eagle Medium (GIBCO) supplemented with 10% defined Bovine Serum (Hyclone, Inc.) and 1% penicillin/streptomycin (GIBCO). Cells were preplated in 100 mm culture dishes such that by the time of transfection the cell number would be about $10^6$ cells per dish. Human genomic DNA (50 µg) and pSV2neo (Southern and Berg, supra) (0.1 µg) were combined in 280 mM NaCl, 10 mM KCl, 1.5 mM $Na_2HPO_4$, 10 mM glucose, 50 mM HEPES, pH 7.05, and an equal volume of 0.25M $CaCl_2$ was added dropwise. The precipitate was kept at room temperature for approximately 30 min before being mixed with culture medium and added to L-M cells for 16 hrs. The precipitate-mixture was then removed and the cells replated into 96-well plates to be cultured in the presence of G418 (GIBCO; 400 µg/ml) until transfectant colonies were well-established.

Typically, each well contained 3–5 colonies following G418-selection. Each well containing transfectant(s) was then trypsinized and replated into separate sets for both assays and cell-stocks.

Example II

Transgenic Cells Containing The Serontonin Transporter a. Screening for Serotonin Uptake

During the initial screening, the entire bank of transfectants were assayed for [$^3$H]-serotonin uptake. To perform the uptake assay on 96-well plates, culture medium of each well was first removed, the cells rinsed twice with oxygenated Ringer's solution (128 mM NaCl, 5.2 mM KCl, 2.1 mM $MgSO_4$, 5 mM glucose, 10 mM HEPES, pH 7.4, supplemented with 0.5 mM ascorbate, 0.5 mM pargyline) and then incubated with 50 µl of Ringer's solution plus 0.1 uM [$^3$H]-serotonin for 40 min at 37° C. The incubation mixture was then removed and each well washed three times before adding 50 µl of alkaline phosphatase buffer: 100 mM Tris, pH 9.5, 100 mM NaCl, 10 mM/$MgCl_2$, 20 µg/ml saponin, 3.2 mg/ml p-nitrophenyl phosphate.

The phosphatase assay was employed as a rapid and convenient measure of relative cell number for each well and served as a normalizing measure to expedite data analyses. The reaction was conducted for 1–2 hrs. at 37° C., and terminated with addition of 100 µl 1% SDS to each well. The extent of the phosphatase reaction for each well was measured at $A_{405}$ nm with an automated ELISA reader. The [$^3$H]-content of each well was then determined by scintillation counting. The data for all the assayed wells were then plotted as the cpm $^3$H of each well versus its corresponding phosphatase reading.

The majority of the data points clustered together in a "main cluster" represented by a linear positive slope. In contrast, the rare high respondents in the assay can be identified as relatively high points above the cluster. The wells containing the high respondents were then expanded from stock plates and rescreened to ensure consistency of high responses.

b. Specificity of Serotonin Transporter

Those wells containing high respondent transgenic cells were also tested with imipramine, a known antagonist of serotonin uptake. For such inhibition assays, the cells in each well were preincubated with Ringer's solution plus 10 µM imipramine at 37° C. for 10 min. [$^3$H]-serotonin was then added to each well to provide a final concentration of 0.1 µM. The cells were incubated at 37° C. for an additional 40 min. Cells demonstrating both high levels of [$^3$H]-serotonin uptake and imipramine antagonism during the second screening were then cloned as single-cell cultures.

Cells derived from the single-cell clones were again tested for both the extent of [$^3$H]-serotonin uptake, as compared with untransformed L-M cells, and imipramine antagonism. In this manner, transformed strain L-S1 was identified as one of the monoclones possessing the desired features.

To further demonstrate that the radioactivity measured in L-S1 represented transport of [$^3$H]-serotonin into these cells, autoradiography was carried out on these cells following incubation with tritiated serotonin. Most of the radioactivity was located inside the cells, rather than binding to the cell surface. When analyzed by reverse-phase HPLC, over 90% of the radioactivity inside the L-S1 cells co-migrated with [$^3$H]-serotonin.

c. Temperature and Ion Dependence

Uptake assays of [$^3$H]-serotonin by L-S1 and L-M were performed with Ringer's solution of varying ionic compositions or different assay temperatures. All assays were performed by incubating the cells with 0.1 µM [$^3$H]-serotonin for 40 min. For $Na^+$-dependence, the uptake level of L-S1 with normal Ringer's solution ("+Na") was set at 100% and used to normalize the uptake levels of L-S1 and L-M assayed in the absence of $Na^+$. Sucrose-supplementation was used to obtain $Na^+$-deficient Ringers ("-Na") by using 256 mM of sucrose to iso-osmotically replace 128 mM of NaCl in making Ringer's solution while all other components remained invariant. Similarly, $Ca^{2+}$-dependence was tested by setting L-S1 uptake levels in normal Ringer's solution ("Na+Ca") at 100% and then comparing to uptake levels in Ringer's solution wherein $Ca^{2+}$ was replaced by $Co^{2+}$ ("Na+Co") or $Mg^{2+}$("Na+Mg"). Uptake into untransformed L-M cells was used as a control.

d. Temperature Dependence

Temperature-dependence was tested by performing the uptake assay at both 37° C. and 0° C. (on ice). Prior to each assay, the cells were first allowed to equilibrate to the desired temperature for 10 min. L-S1 assayed at 37° C. was set as 100% level, against which data obtained for 0° C. were normalized. All data were first converted to cpm/mg protein prior to normalization against L-S1 uptake levels. The results are shown in Table I, below.

TABLE I

ION AND TEMPERATURE DEPENDENCIES OF
[³H]-SEROTONIN UPTAKE BY L-S1

| | | L-S1 (%) | L-M (%) |
|---|---|---|---|
| Sodium: | +Na | 100.00 | 18.90 ± 2.07 |
| | −Na | 12.37 ± 1.66 | 11.46 ± 1.28 |
| Calcium: | Na + Ca | 100.00 | 17.30 ± 1.70 |
| | Na + Co | 97.64 ± 10.62 | 16.12 ± 1.44 |
| | Na + Mg | 98.56 ± 10.09 | 18.48 ± 1.57 |
| Temp.: | 37° C. | 100.00 | 11.70 ± 1.04 |
| | 0° C. | 2.77 ± 0.29 | 1.36 ± 0.07 | e. Specificity of Serotonin Transporters

The specificity of [³H]-serotonin uptake by L-S1 and L-M cells was determined as follows. L-S1 and L-M cells were preplated into 96-well culture plates and assayed by incubating each well with oxygenated Ringer's solution plus 0.1 μM of [³H]-serotonin without or with a competing, unlabelled ligand. The repertoire of competing ligands are as follows: serotonin (5HT); imipramine (IMIP); dopamine (DA); γ-aminobutyric acid; tryptophan; tyrosine; and phenylalanine. Each competing ligand was added to the assay to a final concentration of 10 μM. The assays were conducted for 40 min at 37° C. Following several washes at room temperature with excess Ringer's solution, the cells were lysed with 1% SDS and a fraction of each well-lysate added to ACS scintillant (Amersham Co.) for counting. The remaining lysate of each well was used for protein content determination using the modified Lowry's method or the BCA method. The extent of [³H]serotonin accumulation in each well was then normalized by its protein content and expressed as "cpm/mg protein" for comparison purposes.

The results showed that the untransformed host cell maintained a relatively constant and low level of serotonin uptake. In the transgenic cells, by contrast, with the exception of the presence of IMIP and 5HT, the level of serotonin uptake remained about the same or slightly greater with the various competing ligands. Thus, none of the unrelated ligands had a significant effect on the specific uptake of serotonin by the L-S1 cell.

f. Kinetic Analysis of Serotonin Transporters

Kinetic analyses of [³H]-serotonin uptake by L-S1 were performed. Uptake assays were performed on L-S1 and L-M with [³H]-serotonin at the following concentrations (M): $5 \times 10^{-5}$, $2 \times 10^{-5}$, $10^{-5}$, $5 \times 10^{-6}$, $2 \times 10^{-6}$, $10^{-6}$, $5 \times 10^{-7}$, $2 \times 10^{-7}$. As a control, L-S1 was also assayed at the above-given concentrations in the presence of a 100-fold molar excess of unlabelled serotonin. In each kinetic experiment, identical sets of cells were assayed with the concentration series listed above at both 37° C. and 0° C. All assays were for 10 min, because the velocity of [³H]-serotonin uptake by L-S1 is linear within that time-frame. The measured cpm levels were each converted to mole-equivalents of serotonin based upon the specific activity of the ³H-label, followed by normalization by both protein content and length of assay. Such values (expressed as pmol/min/mg protein) obtained at 0° C. were subtracted from the corresponding values obtained at 37° C. resulting in the specific uptake velocity for each cell-type at a given concentration of radiolabelled serotonin in the absence or presence of excess unlabelled serotonin.

A Michaelis-Menton plot of specific uptake velocity (V) versus [³H]-serotonin concentration (S) for both L-S1 and L-M, was made. Also, the data was analyzed by a Lineweaver-Burk plot by plotting the inverse of the velocity values (1/V) against the inverse of the concentration values (1/S). Data for L-S1, L-S1 with excess unlabelled serotonin and L-M were each fitted to a straight line by linear regression, and in each case the correlation coefficient was 0.99 or higher. With the equation obtained for L-S1 in Lineweaver-Burk transformation, both its x- and y-intercepts were extrapolated and inverted to calculate the $K_m$ and $V_{max}$ for serotonin uptake in the L-S1 cells.

The kinetic analyses showed that the serotonin uptake by L-S1 is a saturable process, in contrast to that by the L-M cell. Likewise, the Lineweaver-Burk plot for uptake into L-S1 yielded a straight line with a discernable negative abscissa-intercept, while L-M cells did not. The abscissa-ordinate-intercepts of transportation into L-S1 cells yielded an apparent $K_m$ of $0.39 \pm 0.096 \times 10^{-6} M$ and a $V_{max}$ of $2.14 \pm 0.55$ pmol/min/mg protein for the serotonin transporter. These values are comparable to those of high-affinity neuronal serotonin uptake systems previously reported (Osborne and Hamon, eds., (1988) *Neuronal Serotonin*, John Wiley and Sons, New York), and support the fact that L-S1 accumulates serotonin by high-affinity mechanisms. This is further supported by the fact that when L-S1 was incubated with Ringer's solution containing [³H]-serotonin and excess unlabelled serotonin, the double-reciprocal plot of transport of L-S1 cell's response shifted to resemble that of transport in the L-M cell.

g. Genomic Analysis of Transgenic Cells Comprising Serotonin Transporters

Genomic blotting analyses with a human Alu sequence probe indicated that L-S1 cells contained integrated human DNA, as indicated by discrete hybridizing DNA fragments within an extensive smear pattern. In contrast, no discernible hybridizing signal was observed with L-M cells. By comparison of the overall hybridizing strength observed for L-S1 DNA with that of known quantities of human genomic DNA, a conservative estimate is that L-S1 contains over $10^6$ bps of stably integrated human DNA.

Example III

Screening For Transgenic Cells Containing The Glycine Transporter a. Screening for Glycine Uptake

The transfectants obtained as described in Example I were screened for uptake of [³H]-Glycine. The [³H]-Glycine-uptake assay was performed in 96-well plates by incubating each well with 50 μl of oxygenated Ringer's buffer (128 mM NaCl, 5.2 mM KCl, 2.1 mM $CaCl_2$, 2.9 mM $MgSO_4$, 5 mM glucose, 10 mM HEPES, pH 7.4), supplemented with 1 mM each of alanine, serine, proline and 0.1M [$^3$H]-Glycine (New England Nuclear, 43.5 Ci/mmol). The incubation was conducted for 40 min at 37° C., and each well then washed three times at room temperature with excess Ringer's buffer. Each well was then incubated with 50 μl of alkaline phosphatase buffer (100 mM Tris, pH 9.5, 100 mM NaCl, 10 mM $MgCl_2$, 20 μg/ml saponin, 3.2 mg/ml p-nitrophenyl phosphate) for 1-2 hours at 37° C. The phosphatase assay was used as a relative assessment of cell number, and used to normalize the level of [$^3$H]-Glycine retained by each cell as described above. The phosphatase reading for each assayed well was plotted versus its corresponding level of [$^3$H]-Glycine-retention and cells identified as high responders cloned and reassayed as described above in Example II for the serotonin transporter. Since all cells possess a low-affinity glycine uptake mechanism for metabolic purposes, only the wells that contained high-responding cells were expanded. These wells were reassayed and ultimately yielded eight clones that manifested relatively high [$^3$H]-Glycine-accumulation levels as compared to L-M cells. We chose one of these clones, L-GLY2, for further analysis. This clone arose from the highest-responding well in the initial screening.

b. Temperature and Ion Dependence of Glycine Transporters (i) Sodium-dependence. Sodium dependence of [$^3$H]-Glycine-uptake was tested by iso-osmotically replacing the assay Ringer's NaCl concentration to variable extents by sucrose as described above in Example II. The resulting iso-osmotic series of Ringer's buffers were each used in uptake assays for L-GLY2 and L-M cells. Each assay was conducted with 0.1 μM [$^3$H]-Glycine (in the presence of 1 mM alanine, proline and serine) at 37° C. for 40 minutes. The amount of protein in each assayed well was determined via a modification of the method of Lowry and used to normalize the level of [$^3$H]Glycine accumulation in the test cells.

When the concentration of NaCl in the assaying Ringer's solution was iso-osmotically replaced by sucrose to varying extents, LGLY2 cells exhibited an almost linear dependence on extracellular [Na+] for [$^3$H]Glycine uptake. L-M cells likewise demonstrated near-linear dependence on extracellular [Na+], but this was not nearly as discernable as that of L-GLY2 because the maximal level of [$^3$H]-Glycine uptake by L-M cells was significantly less than that of L-GLY2 cells. Clearly, L-GLY2 cells exhibited a [$^3$H]-Glycine-uptake mechanism that is sodium-dependent. However, the relatively smaller uptake activities associated with L-M cells also seemed to have a sodium-dependent component.

(ii) Temperature-dependence. The temperature dependence of [$^3$H]-Glycine uptake was determined by assaying both L-GLY2 and L-M cells at 37° C. versus 0° C. (on ice). Each assay was conducted between 0 and 40 min., and [$^3$H]-Glycine accumulation at several timepoints therein was quantitated and normalized by corresponding protein contents. At 37° C., [$^3$H]-Glycine-accumulation by L-GLY2 cells increased almost linearly with incubation times up to 40 minutes. The transport of [$^3$H]-Glycine by L-M cells at 37° C. was significantly less than that of L-GLY2 cells, but nonetheless distinct from uptake activities at 0° C. Thus, while varying in magnitude, both L-GLY2 and L-M cells exhibit temperature-dependence in [$^3$H]-Glycine uptake.

c. Screening for Specificity of Glycine Transporter

L-GLY2 and L-M cells were assayed for the uptake of [$^3$H]-Glycine (0.1 μM) in the presence or absence of competing, unlabelled amino acids or neurotransmitters. Each competing ligand was present in 1000-fold molar excess (100 μM) of the [$^3$H]-Glycine. The competing neurotransmitters used included serotonin, dopamine and γ-aminobutyric acid; the competing amino acids used included tryptophan, tyrosine, glutamine, valine, cysteine, glutamate and lysine. The assays were performed at 37° C. for 40 minutes, and 1 mM alanine, proline and serine was added to the Ringer's buffer.

in the presence of a 1000-fold molar excess of unlabelled neurotransmitter or amino acids, transport of [$^3$H]-Glycine into L-GLY2 cells exhibited no change except in the presence of unlabelled glycine. This indicated that the Glycine-uptake mechanism in L-GLY2 Was specific with regards to its substrate. Uptake of [$^3$H]-Glycine into L-M cells, while lower, was not significantly inhibited by any competing ligand, including unlabelled glycine. These results suggested that the uptake mechanism in L-GLY2 cells is saturable since a 1000-fold excess of Glycine reduced [$^3$H]-Glycine transport into L-GLY2 cells to the same level as that of L-M cells. Thus, L-GLY2 cells are expressing a [$^3$H]-Glycine-uptake mechanism which is neurotransmitter- and amino acid-specific, competable and absent from L-M cells.

d. Kinetic Analysis of Glycine Transporters

Various concentrations of [$^3$H]-Glycine (ranging from 50 nM to 5 μM) were used to assay L-GLY2 and L-M cells for 5 minutes at both 37° C. (total uptake) and 0° C. (non-specific uptake). At each concentration of [$^3$H]-Glycine, both uptake levels were converted to picomole-equivalent of [$^3$H]-Glycine, then normalized by both length of assay and corresponding protein contents to arrive at the uptake velocity values. The nonspecific uptake velocity was then subtracted from the total uptake velocity to yield the specific uptake velocity. The specific uptake velocities and their corresponding [$^3$H)-Glycine concentrations were analyzed by both the Micbaelis-Menten method and the Lineweaver-Burk method. For both analyses, data-points were fitted to either linear or logarithmic functions by computerized algorithms.

We analyzed the kinetic parameters of glycine transport into L-GLY2 and L-M cells. All the kinetic assays were conducted at 5 minutes, because within that timeframe the velocity of [$^3$H]-Glycine uptake by L-GLY2 appeared linear. Assays performed at 37° C. yielded total uptake velocities which, when corrected by subtraction of corresponding values attained at 0° C. (representing nonspecific uptake velocities), resulted in specific uptake velocities. When the assay concentrations of [$^3$H]-Glycine (50 nM to 5 μM) were plotted versus their corresponding specific uptake velocities (as shown in FIG. 5a), the resulting Michaelis-Menten plot indicated that the kinetic profile of L-GLY2 was curvilinear (concave downward). This implied that the [$^3$H]-Glycine-uptake observed for L-GLY2 cells was a kinetically saturable event. L-M, on the other hand, yielded a linear kinetic relationship that was quite diminutive in magnitude when compared with that of L-GLY2. L-M cells exhibited nonsaturable kinetics, within the range of [$^3$H]-Glycine concentrations employed. Lineweaver-Burk transformations of the kinetic data resulted in linear relationships of transport for both L-GLY2 and L-M cells. The line corresponding to L-G2 cells has a discernable positive ordinate-intercept and a negative abscissa-intercept. In contrast, the line representing L-M cells had neither. This was a clear demonstration that L-GLY2 cells exhibited a discernable [$^3$H]-Glycine-uptake mechanism which was saturable and of high affinity. This transporter mechanism for [$^3$H]-Glycine was absent from L-M cells, since, within the assayed concentration range of [$^3$H]-Glycine, L-M cells exhibited neither discernable affinity nor capacity measures.

The Lineweaver-Burk plot for L-GLY2 yielded an apparent $K_m$ of $1.50 \mp 0.20 \times 10^{-6}$M and a $V_{max}$ of $10.19 \mp 3.32$ pmol/min/mg protein. As shown in Table II, these values are quite comparable published values for high-affinity glycine uptake in the CNS (Chin & Lam (1980) *J. Physiol.* 308:185–195; Voaden, Marshall & Murani (1974) *Brain Res.* 67:115–132: Muller & Snyder (1978) *Brain Res.* 143:487–498; Mayor, Marvizon, Aragon, Gimenez & Valdivieso (1981) *Biochem. J.* 198:535–541; Hardy, Barton, Lofdahl, Cheetham, Johnston & Dodd (1986) *J. Neurochem* 47:460–467; Zafra & Gimenez (1986) *Brain Res.* 397:108–116; Debler & Lajtha (1987) *J. Neurochem.* 48:1851–1856; Yorek, Dunlap & Ginsberg (1987) *J. Biol. Chem.* 262:10986–10993; Hendrickson, Koontz, Pourcho, Sarthy & Goebel (1988) *J. Comp. Neurol.* 273:473–487) and definitively established L-GLY2 cells as possessing a high-affinity glycine uptake mechanism which is absent from L-M cells.

TABLE II

| TISSUE/SYNAPTO-SOME/CELL | $K_m$ (μM) | $V_{max}$ (pmol/mg/min) |
|---|---|---|
| L-G2 | 1.50 ± 0.20 | 10.19 ± 3.32 |
| Tissue: | | |
| goldfish retina | 8.08 ± 0.70 | 8.71 ± 0.54 |
| monkey retina | 2.50 ± 0.90 | 3.30 ± 1.60 |
| frog retina | >4.70 | |
| Membrane Preparations: | | |
| human brain (post-mortem) | 35 ± 19 | 55 ± 25 |
| C6 glioblastoma | 100 | 320 |
| frog brain | 24.80 ± 1.40 | 1.14 ± 0.06 |
| frog spinal cord | 29.00 ± 0.70 | 1.52 ± 0.03 |
| rat brain | 34.00 ± 1.30 | 0.48 ± 0.07 |
| rat spinal cord | 46.50 ± 1.60 | 1.43 ± 0.02 |
| chicken brain | 37.00 ± 2.00 | 0.32 ± 0.01 |
| chicken spinal cord | 41.80 ± 1.00 | 0.65 ± 0.02 |
| mouse cerebral cortex | 15.20 ± 2.00 | 340 ± 70 |
| mouse pons-medulla-spinal cord | 27.60 ± 2.60 | 3100 ± 100 |
| Cell: | | |
| Y79 retinoblastoma | 24.40 ± 2.60 | 138.40 ± 12.40 |

In another kinetic analysis, the assaying concentrations of [$^3$H]-Glycine were increased to between 1 μM and 100 μM. The resulting kinetic profiles for both L-GLY2 and L-M cells were saturable, with L-GLY2 cells exhibiting slightly higher uptake velocities than L-M cells. Lineweaver-Burk transformations of this set of uptake data yielded two overlapping lines having comparable intercepts on both axes. The affinity and capacity measures for these uptake events were comparable to those of amino acid uptake systems that are present in all cells (Oxender & Christensen (1963) *J. Cell Biol.* 238:3686–3699; Revsin & Morrow (1976) *Exp. Cell Res.* 100:95–103; Sepulveda & Smith (1978) *J. Physiol.* 282:73–90). Thus, while both L-GLY2 and L-M cells possess low affinity amino acid uptake mechanisms, L-GLY-2 cells in addition manifested a distinctly different, high-affinity Glycine-uptake mechanism.

e. Genomic Analysis of Transgenic Cells Comprising The Glycine Transporter

Genomic DNA was extracted from L-GLY2 cells, digested to completion by restriction endonucleases BamHI and EcoRI (New England BioLabs), and electrophoretically separated on a 0.8% agarose gel. Following depurination and denaturation, the DNA fragments were absorbed onto Nytran filters (Schleicher & Schuell) and hybridized with the 300 bp human Alu-probe isolated by BamHI-digestion of PBLUR-8 (Jelinek, Toomey, Leinwand, Duncan, Biro, Choudary, Weissman, Rubin, Houck, Deininger & Schmid (1980) *Proc. Natl. Acad. Sci. USA* 77:1398–1402). The probing Alu insert was labelled by random-priming (Feinberg & Vogelstein (1983) *Anal. Biochem.* 132:6–13) with [α-$^{32}$P]dCTP (New England Nuclear, 3000 Ci/mmol).

Both the hybridization and subsequent washings were performed at very high stringencies, and the resulting blot exposed at $-70°$ C. to Kodak XAR5 film in the presence of an intensifying screen (DuPont). The resulting autoradiogram illustrated the presence of human Alu sequences within the L-GLY2 cells, showing that integration of human DNA into the L-M genome had occurred during transfection. EcoRI-digestion of L-GLY2 DNA resulted in two closely-spaced hybridizing bands, while BamHI-digestion resulted in three discernable bands. Each of these digestions indicated that the hybridizing bands comprised approximately $2 \times 10^4$ bp of human DNA per L-GLY2 genome. Parallel hybridization of L-M genomic DNA revealed no discernable hybridizing signal. This is consistent with the Alu sequences being restricted to primate species (Houck, Rinehart & Schmid (1979) *J. Mol. Biol.* 132:289–306). The correlation between both the presence of a high-affinity Glycine-uptake mechanism and the integration of human DNA into the genome of L-GLY2 cells indicated that the high-affinity glycine uptake mechanism in L-GLY2 results from the expression of stably-integrated human gene(s) for the glycine transporter.

Example IV

Screening For Transgenic Cells Comprising The Dopamine Transporter a. Screening of Transfectants for [$^3$H]-Dopamine Uptake Cell transfectants obtained as described in Example I were trypsinized and replated into separate sets for assay and cell-stocks. During the initial screening, the entire bank of transfectants was assayed for [$^3$H]-dopamine uptake. To carry out the uptake assay on 96-well plates, culture medium from each well was first removed, the cells rinsed with 200 μl of oxygenated Ringer's solution (128 mM NaCl, 5.2 mM KCl, 2.1 mM CaCl$_2$, 2.9 mM MgSO$_4$, 5 mM glucose, 10 mM HEPES, pH 7.4, supplemented with 1 mM ascorbate, 10 μM pargyline) and then incubated 40 minutes at 37° C. with 50 μl Ringer's solution plus 0.1 μM [³H]-dopamine (New England Nuclear; 40 Ci/mmol). The incubation mixture was then removed and cell plates were placed on ice for 30 minutes before three 2 minute washings with 100 μl ice-cold isotonic NaCl. Each well was then incubated with 50 μl of alkaline phosphatase assay mixture (100 mM Tris, pH 9.5, 100 mM NaCl, 10 mM MgCl₂, 20 mg/ml saponin, 1.32 mg/ml P-nitrophenyl phosphate) as described in Example II.

The wells containing the high responders, high ³H-dopamine cpm as normalized by the phosphatase assay, were then expanded from stock plates and rescreened to ensure recurrence of high responses. Additionally, these secondary clones were rigorously assayed with 0.1 μM [³H]-dopamine alone or following a preincubation period of 10 minutes with 10 μM unlabelled dopamine or 125 μM benztropine, to confirm the presence of a specific uptake mechanism.

Wells which consistently exhibited high dopamine uptake and were inhibited by both unlabelled dopamine and benztropine were used to generate single cell cultures. To ensure representative populations of monoclones in sufficient numbers, at least four 96 well plates of monoclones were generated from each secondary well. An 80% success rate for generation of single cell cultures was attained by plating an average of 75 cells per 96 well plate.

After initial plating of individual cells, each well was carefully monitored for the presence of only single clones. Wells were monitored at weekly intervals and only those clones which had attained confluence were trypsinized and replated at any one time. This was a necessary step to obviate the potential lethal effects of premature trypsinization. Original plates were maintained for 25-30 days to allow monoclones to become confluent.

As monoclones became confluent, they were replated and assayed in duplicate; stock wells were maintained in culture until screening of the entire plate was completed. Screening of monoclones in duplicate was performed to reduce the probability of false positives. Only those monoclones which showed good agreement between duplicate assays were retained for further analysis by competitive assays with unlabelled dopamine and benztropine. Two clones showing specific uptake of [³H]-dopamine were identified: L-D1 and L-D2.

b. Rate and Kinetics of Dopamine Uptake

Rates of dopamine uptake by putative transgenic clones and untransfected cells were determined by incubation of the cells for selected intervals from 0 to 40 minutes at 37° C. Uptake rates were simultaneously determined with 0.1 μM [³H]dopamine alone or following preincubation with 10 μM unlabelled dopamine and 125 μM benztropine. For L-D2, uptake was linear from zero to 10 minutes after addition of [³H]-dopamine. Kinetic analaysis using concentrations ranging from $7.5 \times 10^{-7}$ to $1.0 \times 10^{-8}$M [³H]-dopamine were carried out for 10 minutes at both 37° C. and 4° C. After 10 minutes, the Ringer's solution containing [³H]-dopamine was removed, and the cells were allowed to cool on ice for 30 minutes. Following three 2-minute washings with ice-cold isotonic NaCl, the cells were dissolved in 100 μl of 1% SDS. Cell-associated radioactivity in L-D2 measured at 4° C. was significantly lower than that measured at 37° C. The initial uptake velocity was determined by subtracting initial velocity at 4° C. from that measured at 37° C, each based on the specific activity of the ³H label, incubation time, and protein concentration (determined by the method of Lowry) (Lowry, Rosebrough, Farr & Randall (1961) *J. Biol. Chem.* 193:256). Kinetic data were expressed in the form of a Michaelis-Menten plot or a Lineweaver-Burk plot of inverse initial velocities versus inverse concentrations using linear regression analysis.

c. Sodium Ion Dependence of Dopamine Transporters

Sodium ion dependence will be determined by incubating putative transgenic clones and untransfected cells at various concentrations of Na⁺ (0 to 128 mM) in oxygenated Ringer's solution. Sodium ion will be iso-osmotically replaced by an appropriate concentration of sucrose. For total replacement of Na⁺, 256 mM sucrose will be utilized.

d. Autoradiographic Analysis

Untransfected cells and L-D2 cells will be plated in 100 mm dishes and assayed for uptake with 0.1 μM [³H]-dopamine for 20 minutes at 37° C. Following three washes with ice cold isotonic NaCl, cells in each plate will be transferred to microfuge tubes, and will be resuspended and pelleted twice in cold NaCl. The cell pellets will be fixed with 4% paraformaldehyde (at 4° C. for 16 hours) before being embedded in EPON-aryldite. Ultramicrotome sections of 1μ thickness will be obtained for each cell pellet and coated with NTB-2 nuclear tract emulsion (Polyscience). The slides will be maintained in the dark at 4° C. for up to six weeks before development.

e. Genomic Blotting Analysis

Genomic DNAs for each cell line will be purified by SDS-phenol extraction. Each sample will be digested with excess restriction endonucleases (New England Biolabs or Promega Biotec) and electrophoresed through agarose gels along with size markers (Hind III/EcoRl digested lambda DNA). DNA samples will be transferred from gels orthogonally onto Nytran filters (Schleicher & Schuell). The human Alu sequence insert will be isolated by BamHI -digestion of pBLUR-8 (Jelinek, Roomey, Leinwand, Duncan, Biro, Choudary, Weissmann, Rubin, Houck, Deininger & Schmid (1980) *Proc. Nat'l. Acad. Sci. USA* 77:1398) labelled with [³²P]-dCTP (New England Nuclear, 3000 Ci/mmol) by random priming (Feinberg & Vogelstein (1983) *Anal. Biochem* 132:6) and used as a hybridization probe. Both the hybridizations and subsequent washings will be performed under very stringent conditions and the resulting blots exposed to Kodak XAR-5 films at −70° C. with intensifying screens.

Example V

Assessment Of Putative Clones As Models Of High-Affinity Dopamine Transport By Using Specific Antagonists a. Screening for Agonists and Antagonists of Dopamine Uptake A number of centrally-acting drugs, including anti-Parkinsonian agents, anti-histamines, tricyclic antidepressants, and phenothiazines, inhibit catecholamine uptake in synaptosomes prepared from various areas of rat brain (Horn, Coyle & Synder (1971) *Molec. Pharmacol.* 7:66). Many of these drugs act as noncompetitive, reversible inhibitors of dopamine uptake by dopaminergic neurons in the corpus striatum where dopamine is the predominant catecholamine. For a transporter, the $IC_{50}$ value is the concentration of inhibitor required to inhibit uptake by 50% as compared to controls without inhibitor. $IC_{50}$ values will be determined for at least four known inhibitors of dopamine uptake: benztropine, diphenyl-pyraline, chlorocyclozine, and nortriptyline, using log probit plots in which the log of percent inhibition of uptake is plotted against inhibitor concentration. The percentage inhibition of uptake will be determined by using at least three different concentrations of inhibitor ranging from $10^{-7}$ to $10^{-5}$M by assaying L-D1 and L-D2 cells in quadruplicate at 0.1 µM [$^3$H]-dopamine and at 37° C. Nonspecific or low affinity binding will be determined by carrying out simultaneous incubations at 0° C. Untransfected LM cells will be used as negative controls. The $IC_{50}$ values obtained from these studies will be compared to those reported for striatal dopaminergic neurons (Horn, Coyle & Synder (1971) *Molecul. Pharmacol.* 7:66). These data should indicate the extent to which clones mimic the behaviour of systems known to possess a high affinity dopamine transport mechanism. Other drugs may then be compared to the known inhibitors, for their ability to block the dopamine transporter.

Example VI

Characterization Of Dopamine Transporter a. Screening for Specificity of Dopamine Transporter The specificity of L-D1 and L-D2 cells for dopamine transport will be determined via competition assays involving selected amino acids—tyrosine, tryptophan, phenylalanine; amino acid derivatives, namely tyramine and L-dopa, and other neurotransmitters including γ-aminobutyric acid (GABA), serotonin, and glycine and norepinephrine. Incubations at 37° C. will be performed utilizing 0.1 µM [$^3$H]-dopamine and 10 µM concentrations of each of the potential ligands listed for predetermined periods of time optimum for these studies. All data will be normalized for protein concentration. Untransfected L-M cells will be used as negative controls. Incubations will be carried out at 37° C. and all data will be normalized for protein concentration.

b. Kinetic Analysis of the Dopamine Transporter

Plasma membrane fractions from untransfected cells and putative clones will be prepared by the method of Ross et al. (Ross, Maguire, Sturgill, Bietmen & Gilman (1977) *J. Biol. Chem* 252:5761) and enriched by centrifugation on discontinuous gradients of sucrose from 30% to 50%. The concentrations of sucrose will be determined with the aid of an Abbe refractometer and fractions obtained at each gradient step will be assayed for [$^3$H]-dopamine affinity. Assays utilizing 150–200 µg of protein will be performed in triplicate at 10, 50 and 100 nM [$^3$H]-dopamine in the absence and presence of excess ligand to determine specific binding. Free and bound ligand will be separated by the charcoal adsorption procedure or by the hydroxylapatite method of Erdos et al. (Erdos, Best-Belpomme & Bessada (1970) *Anal. Biochem.* 37:244). The gradient fraction exhibiting the highest specific saturable binding of dopamine will be used to determine the dissociation constant and the number of binding sites by the method of Scatchard (Scatchard (1949) *Ann. N.Y. Acad. Science* 51:660). Binding assays will be repeated with membrane fractions solubilized in an appropriate detergent such as Triton X-100.

Example VII

Purification Of Dopamine Transporters And Generation Of Specific Antibody Probes The plasma membrane fraction exhibiting the highest affinity for dopamine (as determined above) will be used as a source of transporter for further purification by conventional chromatographic methods currently used in our laboratory.

Specific antibody probes will be generated to facilitate the formulation of purification protocols:

a. Antibody Production in Syngeneic Mice

Mice of the C3H/An strain (Kuckler & Merchant (1956) *Proc. Soc. Exp. Biol. Med.* 92:803) from which naive fibroblasts originated will be injected with L-D1 and L-D2 cells. Antisera will be screened for antibodies to surface antigens, encoded by transfected human genes, by ELISA (Engrall & Perlmann (1972) *J. Immunol.* 109:129). Use of antisera for purification of antigens by affinity chromatography will depend on antibody titer and amount of antisera which can be obtained.

b. Antibody Directed Against Common Antigens

Antisera will be obtained from New Zealand white rabbits injected with cell lysates and plasma membrane preparations from untransfected cells. The antiserum produced will contain antibodies produced against common antigens of both untransfected cells and L-D1 and L-D2, but not against those proteins encoded by transfected human genes. Immunoglobulins will be separated from total serum by ammonium sulfate precicpitation at 50% saturation. Resuspended immunoglobulins will be used to precipitate common antigens from solubilized cell lysates and plasma membrane preparations. Proteins remaining in the supernatant after several rounds of precipitation will be assayed for their capacity to bind [H$^3$]-dopamine and analyzed by two dimensional gel electrophoresis using the method of O'Farrell (O'Farrell (1975) *J. Biol. hem.* 250:4007).

For two dimensional electrophoresis, cells will be transferred to a minimum essential methionine-culture medium and incubated with 10–50 µCi of S$^{35}$-methionine per ml of media for 20–24 hours. Cells will be harvested and suspended in SDS solubilization buffer (Anderson, Anderson & Tollaksen, *Argonne Nat'l Lab.*, Publication 79-2) (0.05M CHES pH 9.5, 2% SDS, 10% glycerol, 2% 2-mercaptoethanol). Samples will be centrifuged at 100,00×g to remove insoluble material and supernatant will be treated with antiserum described above. Proteins remaining in the supernatant after treatment with antiserum will be concentrated so that approximately 40 µg containing 100,000 cpm in 25 µl will be loaded in the first dimension. Upon completion of electrophoresis in the second dimension, gels will be fixed, patterns will be evaluated visually from staining and from autoradiographs. Peptides present in lysates or membranes from putative transgenic clones but not in preparations from control cells will be used as antigens for further specific antibody production.

It is evident from the above results that novel methods and compositions are provided for studying neurotransmitter transport in cell culture. Thus, an important new tool is provided for dissecting the mechanism of neurotransmitter transport, while also allowing for rapid screening of a large number of compounds for their ability to bind to the receptor and be transported intracellularly or compete with compounds bound by the receptor.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An in-vitro cell culture consisting essentially of transgenic mammalian cells comprising:
   a DNA fragment comprising human DNA encoding a neurotransmitter transporter, said transporter being characterized as capable of transporting said neurotransmitter into said cells.

2. The cell culture according to claim 1, wherein said cells are of the genus rodentiae.

3. The cell culture according to claim 1, wherein said cells are other than neuronal cells.

4. The cell culture according to claim 1, wherein said neurotransmitter is 5-hydroxytryptamine, dopamine or glycine.

5. An in-vitro composition consisting essentially of:
   a plurality of transgenic primate cells comprising human DNA encoding a neurotransmitter transporter, wherein uptake of a neurotransmitter into said cells via said transporter is characterized as sodium ion dependent, saturable and temperature sensitive with the proviso that when said primate cells are human cells, said DNA is heterologous to said cells.

6. The composition according to claim 5, wherein said cells are further characterized as capable of being grown in vitro.

7. The composition according to claim 5, wherein said uptake is further characterized as being at least substantially inhibited by known agonists or antagonists of said neurotransmitter.

8. The composition according to claim 5, wherein said uptake is further characterized as being of high affinity.

9. The composition according to claim 6, wherein said cells are mouse fibroblast cells.

10. The composition according to claim 9, wherein said cells further comprise a cytotoxic agent resistance gene and are resistant to said cytotoxic agent.

11. A method for determining whether a candidate compound is an inhibitor of neurotransmitter uptake, said method comprising:
    contacting a cell culture according to claim 1 with:
    (a) said candidate compound and a neurotransmitter comprising a detectable label; or
    (b) a neurotransmitter comprising a detectable label;
    (c) normalizing the amount of detectable label in (a) and (b); and
    comparing the amount of normalized label detectable in (a) with the amount of normalized label detectable in (b), wherein (b)>(a) is indicative that said candidate compound is an inhibitor of neurotransmitter uptake.

12. The method according to claim 11, wherein said cells in (a) are contacted with said compound prior to being contacted with said neurotransmitter.

13. The method according to claim 11, wherein said neurotransmitter is 5-hydroxytryptamine, dopamine or glycine.

14. A method for determining whether a candidate compound is an agonist or an antagonist of neurotransmitter uptake, said method comprising:
    contacting a cell culture according to claim 1, with:
    (a) said candidate compound and a neurotransmitter comprising a detectable first label; or
    (b) a neurotransmitter comprising a first label; or
    (c) said candidate compound comprising a detectable second label and unlabelled neurotransmitter; or
    (d) said candidate compound comprising a detectable second label;
    wherein said first label and said second label may be the same or different;
    (e) normalizing the amount of label detectable in (a), (b), (c) and (d); and
    comparing the amount of normalized label detectable in (a) with the amount of normalized label detectable in (b); and the amount of normalized label detectable in (c) with the amount of normalized label detectable in (d), wherein (b)>(a) and (d)>(c) is indicative that said candidate compound is an agonist of neurotransmitter uptake, and (b)>(a) and (d) not>(c) is indicative that said candidate compound is an antagonist of neurotransmitter uptake.

15. An in-vitro cell culture and cultures derived therefrom consisting essentially of:
    non-human mammalian cells containing a human DNA sequence encoding a neurotransmitter transporter, wherein said cells are characterized as capable of at least substantially specifically transporting a neurotransmitter of interest as a result of expression of said DNA sequence, said transporting being sodium ion dependent, saturable and temperature sensitive.

16. An in-vitro culture of non-human mammalian cells and cells derived therefrom comprising:
    a human DNA sequence encoding a neurotransmitter transporter, wherein said cells are characterized as capable of at least substantially specifically transporting a neurotransmitter of interest as a result of expression of said DNA sequence, said transporting being sodium ion dependent, saturable and temperature sensitive.

17. An in-vitro composition consisting essentially of:
    a plurality of non-human mammalian cells containing a neurotransmitter transporter as a result of transformation with a DNA fragment comprising a human DNA sequence encoding said transporter, wherein uptake of a neurotransmitter into said cells via said transporter is characterized as being sodium ion dependent, saturable and temperature sensitive.

* * * * *